(12) United States Patent
Huang et al.

(10) Patent No.: US 8,637,467 B2
(45) Date of Patent: Jan. 28, 2014

(54) PHARMACEUTICAL BEING USED FOR TREATING CANCER AND FIBROSIS DISEASE AND THE COMPOSITION AND USES THEREOF

(75) Inventors: Lan Huang, Shanghai (CN); Hua Zhou, Shanghai (CN); Shengtao Yuan, Jiangsu (CN)

(73) Assignee: Wuxi MTLH Biotechnology Co., Ltd., Wuxi (CN)

( * ) Notice: Subject to any disclaimer, the term of this patent is extended or adjusted under 35 U.S.C. 154(b) by 152 days.

(21) Appl. No.: 13/123,424

(22) PCT Filed: Sep. 21, 2009

(86) PCT No.: PCT/CN2009/074048
§ 371 (c)(1),
(2), (4) Date: Jul. 5, 2011

(87) PCT Pub. No.: WO2010/040305
PCT Pub. Date: Apr. 15, 2010

(65) Prior Publication Data
US 2011/0263513 A1 Oct. 27, 2011

(30) Foreign Application Priority Data
Oct. 9, 2008 (CN) .......................... 2008 1 0200937

(51) Int. Cl.
*A61K 38/16* (2006.01)
*C07K 14/00* (2006.01)

(52) U.S. Cl.
USPC ....... 514/19.8; 514/19.3; 514/19.4; 514/21.3; 530/324

(58) Field of Classification Search
None
See application file for complete search history.

(56) References Cited

U.S. PATENT DOCUMENTS

| | | | | |
|---|---|---|---|---|
| 5,595,756 A | * | 1/1997 | Bally et al. | 424/450 |
| 2003/0211994 A1 | * | 11/2003 | Li et al. | 514/12 |

FOREIGN PATENT DOCUMENTS

| | | |
|---|---|---|
| CN | 101392026 | 3/2009 |
| WO | WO 00/18212 | 4/2000 |
| WO | WO 00/37641 | 6/2000 |
| WO | WO 2004/070018 | 8/2004 |
| WO | WO 2007/022287 | 2/2007 |

OTHER PUBLICATIONS

Definition of derivative from http://cancerweb.ncl.ac.uk/omd/about.html, pp. 1-5. Accessed Jul. 7, 2005.*
Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Cancer Drug Design and Discovery Neidle, Stephen, ed. (Elsevier/Academic Press, 2008) pp. 427-431.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of Escherichia coli maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Extended European Search Report issued in European patent application No. 09 818 769.3, dated Feb. 24, 2012.
Fredriksson et al., "Structural requirements for activation of latent platelet-derived growth factor CC by tissue plasminogen activator," Journal of Biological Chemistry, 280(29):26856-26862, 2005.
Li et al., "PDGF-C is a new protease-activated ligand for the PDGF alpha-receptor," Nature Cell Biology, 2(5):302-309, 2000.
Reigstad et al., "Platelet-derived growth factor (PDGF)-C, a PDGF family member with a vascular endothelial growth factor-like structure," Journal of Biological Chemistry, 278(19):17114-17120, 2003.
Reigstad et al., "Structural and functional specificities of PDGF-C and PDGF-D, the novel members of the platelet-derived growth factors family," FEBS Journal, 272(22):5723-5741, 2005.
Campbell et al., "Platelet-derived growth factor C induces liver fibrosis, steatosis, and hepatocellular carcinoma," Proc. Natl. Acad. Sci., 102(9): 3389-3394, 2005.
Gilbertson et al., "Platelet-derived growth factor C (PDGF-C), a novel growth factor that binds to PDGF alpha and beta receptor," J. Biol. Chem., 276(29):27406-27414, 2001.
International Preliminary Report on Patentability issued in PCT/CN2009/074048, dated Apr. 12, 2011.
International Search Report issued in PCT/CN2009/074048, dated Dec. 31, 2009.

* cited by examiner

*Primary Examiner* — Julie Ha
(74) *Attorney, Agent, or Firm* — Fulbright & Jaworski LLP

(57) ABSTRACT

Provided is the composition of a peptide and its mutagenic version, or other derivatives with the same 3-D structure with activity to bind the extracellular domain of PDGFR-α, or -β, but does not dimerize by itself, wherein said peptide comprises the sequence shown as SEQ ID NO: 1, 2 or 3. Also provided is the composition of the nucleotide sequence encoding said peptide and its derivatives, and the usage of said peptide and derivatives of the peptide in preparation of medicine for the prevention and treatment of fibrosis diseases, such as liver, kidney, and lung fibrosis, primary cancer, and cancer metastasis, especially stomach cancer, liver cancer, breast cancer, and lung cancer.

12 Claims, 5 Drawing Sheets

| sample state | Solid | Estimated M.W. | 52000 |
|---|---|---|---|
| Equipment | ABI491A | Equipment Company | AB Company |

| | Seq. No. | Amino Acid | Seq. No. | Amino Acid |
|---|---|---|---|---|
| | 1 | S | 2 | K |
| | 3 | V | 4 | T |
| | 5 | K | 6 | K |
| | 7 | Y | 8 | H |
| | 9 | E | 10 | V |
| | 11 | L | 12 | Q |
| | 13 | L | 14 | R |
| | 15 | P | 16 | K |
| | 17 | T | 18 | G |
| | 19 | V | 20 | R |
| Sequencing Result | 21 | C | 22 | L |
| | 23 | H | 24 | K |
| | 25 | S | 26 | L |
| | 27 | T | 28 | D |
| | 29 | V | 30 | A |
| | 31 | L | 32 | E |
| | 33 | H | 34 | H |
| | 35 | E | 36 | E |
| | 37 | x | 38 | D |
| | 39 | x | 40 | Y |
| | 41 | x | 42 | R |
| | 43 | G | 44 | S |
| | 45 | T | 46 | C |
| | 47 | C | 48 | |
| Notes | NH2-S-K-V-T-K-K-Y-H-E-V-L-Q-L-R-P-K-T-G-V-R-C-L-H-K-S-L-T-D-V-A-L-E-H-H-E-E-x-D-x-Y-x-R-G-S-T-C-C (X under normal cond. is C) | | | | peptide obtained from example 1 1uM

SEQUENCE LISTING

<160> NUMBER OF SEQ ID NOS: 3

<210> SEQ ID NO 1
<211> LENGTH: 47
<212> TYPE: PRT
<213> ORGANISM: Homo sapiens

<400> SEQUENCE: 1

Ser Lys Val Thr Lys Lys Tyr His Glu Val Leu Gln Leu Arg Pro Lys
1               5                   10                  15

Thr Gly Val Arg Gly Leu His Lys Ser Leu Thr Asp Val Ala Leu Glu
            20                  25                  30

His His Glu Glu Cys Asp Cys Val Cys Arg Gly Ser Thr Gly Gly
        35                  40                  45

<210> SEQ ID NO 2
<211> LENGTH: 105
<212> TYPE: PRT
<213> ORGANISM: Homo sapiens

<400> SEQUENCE: 2

Leu Thr Glu Glu Val Arg Leu Tyr Ser Cys Thr Pro Arg Asn Phe Ser
1               5                   10                  15

Val Ser Ile Arg Glu Glu Leu Lys Arg Thr Asp Thr Ile Phe Trp Pro
            20                  25                  30

Gly Ser Leu Leu Val Lys Arg Cys Gly Gly Asn Cys Ala Ser Cys Leu
        35                  40                  45

His Asn Cys Asn Glu Cys Gln Cys Val Pro Ser Lys Val Thr Lys Lys
    50                  55                  60

Tyr His Glu Val Leu Gln Leu Arg Pro Lys Thr Gly Val Arg Gly Leu
65                  70                  75                  80

His Lys Ser Leu Thr Asp Val Ala Leu Glu His His Glu Glu Cys Asp
            85                  90                  95

Cys Val Cys Arg Gly Ser Thr Gly Gly
            100                 105

<210> SEQ ID NO 3
<211> LENGTH: 80
<212> TYPE: PRT
<213> ORGANISM: Homo sapiens

<400> SEQUENCE: 3

Thr Asp Thr Ile Phe Trp Pro Gly Ser Leu Leu Val Lys Arg Cys Gly
1               5                   10                  15

Gly Asn Cys Ala Ser Cys Leu His Asn Cys Asn Glu Cys Gln Cys Val
            20                  25                  30

Pro Ser Lys Val Thr Lys Lys Tyr His Glu Val Leu Gln Leu Arg Pro
        35                  40                  45

Lys Thr Gly Val Arg Gly Leu His Lys Ser Leu Thr Asp Val Ala Leu
    50                  55                  60

Glu His His Glu Glu Cys Asp Cys Val Cys Arg Gly Ser Thr Gly Gly
65                  70                  75                  80

PHARMACEUTICAL BEING USED FOR TREATING CANCER AND FIBROSIS DISEASE AND THE COMPOSITION AND USES THEREOF This application is a national phase application under 35 U.S.C. §371 of International Application No. PCT/CN2009/074048 filed 21 Sep. 2009, which claims priority to Chinese Patent Application No. 20080200937.8 filed on 9 Oct. 2008. The entire text of each of the above-referenced disclosures is specifically incorporated herein by reference without disclaimer.

FIELD OF TECHNOLOGY

The present invention relates to the composition of a peptide and its active derivatives with the same 3-D structure in the prevention and treatment of fibrosis diseases, primary cancer, and cancer metastasis. This peptide and its active derivatives inhibit PDGFR signaling by blocking the binding of PDGFs with their receptors at the extracellular level.

BACKGROUND OF THE INVENTION

1) Fibrosis Diseases and PDGF and PDGFR Family

When stimulated or damaged by outside factors, organ (or tissue) will form abnormal fibrosis, such as liver fibrosis, cardiac muscle, peritonaeum fibrosis, intervertebral fibrosis, bone marrow fibrosis, lung fibrosis, kidney fibrosis etc. Abnormal fibrosis could cause many diseases. For example, liver fibrosis causes liver cirrhosis, and liver cancer. Kidney fibrosis leads to malignant transformation of various renal tubule and tubulointerstitial Lesion, and is one of the major reasons for late-stage kidney failure. Lung fibrosis causes lung compliance decrease, lung capacity decrease, diffusion dysfunction decrease, VA/VQ imbalance, and finally lung failure, with lower than 50% of 5 year survival rate.

Research demonstrates that the cause of liver fibrosis, bone marrow fibrosis, lung fibrosis, and kidney fibrosis is related to the overexpression of PDGF family and PDGFR.

Three steps in chronic liver diseases are 1) hepatitis, 2) liver fibrosis, and 3) liver cirrhosis. Chronic fibrosis disrupts the essential structure of liver sinusoids, impairing the function of the liver and eventually leading to cirrhosis. If liver fibrosis cannot be treated, it will eventually lead to liver cirrhosis.

When liver cells die or affected by inflammation, Liver fibrosis forms by imbalance of extracellular matrix (ECM), with a bias toward deposition of fibrillar (type I) collagen within the subendothelial space of Disse. Viral hepatitis, chemical insult, and fatty liver all could cause liver fibrosis, a damaging liver disease. According to epidemic disease research reports, ¼ of hepatitis patients infected by virus will become chronic hepatitis patients. Among all chronic hepatitis patients, 5-20% will develop liver cirrhosis. Among liver cirrhosis patients, 50% of them will eventually develop liver cancer. Thus when liver fibrosis is formed, it is very hard to be reversed at normal condition. Liver fibrosis will lead to liver malfunction, which damages human health.

Although many different kinds of liver cells affect liver fibrosis, hepatic stellate cells (HSC) has essential function to the disease development.

In normal liver, the amount of HSC is quite small, with ratio of HSC:normal liver cells=1:20, and HSC's volume is 1.4% of the liver volume. HSC mainly has the following function: 1) store and metabolize Vitamin A; 2) Synthesize and secret small amount of ECM deposition, mainly Type I, III, and VI collagen; 3) break out to surround SEC (sinusoidal endothelial cells), support endothelial cells, and regulate sinusoid size; and 4) synthesize non-collagen glycoprotein and protein carbohydrate.

Research demonstrates that liver fibrosis is caused by activation of HSC in liver tissue. Over-expression of PDGF-C and PDGF receptors (PDGFR) at mRNA and protein levels is one of the earliest events. Activated HSC and myofibrobalsts produce a number of profibrotic cytokines and growth factors that perpetuate the fibrotic process through paracrine and autocrine effects. PDGF-BB and TGF-$\beta$1 are two key factors in fibrogenesis. Increased expression of both growth factors induces overexpression of collagen, and TIMP-1 and TIMP-2 secretion which inhibits collagen breakdown. All of these events lead to imbalance of ECM deposition and large deposition of collagen in liver tissue, which causes HSC to become myofibroblast-like (MFB). It leas to the surrounding liver cells wrapped by collagen, so that these liver cells lose normal function.

Liver fibrosis development leads to liver tissue hyperemia and liver steatosis formation, and eventually liver cancer. Thus any medication which can prevent or treat liver fibrosis is a good adjunct therapy for liver cancer.

Platelet-derived growth factor (PDGF) family has 4 types: PDGF-A, -B, -C, and -D), and two receptors: PDGFR-$\alpha$ and -$\beta$. They play an important role in wound healing, atherosclerosis, fibrosis, and malignancy. PDGF-C is the cytokine which was discovered most recently. It forms homodimer PDGF-CC, and has more potent biological activity towards mesenchymal cells than that of PDGF-AA, PDGF-AB, and PDGF-BB (Gilbertson et. al. JBC 276(29), 27406 (2001)).

Using real time PCR technology, Breitkopf team studied the mRNA expression profile of PDGF-C in transdifferentiating primary cultured HSC cells, an in vitro model system of hepatic fibrogenesis, either with or without stimulation of the cells with PDGF-BB or TGF-$\beta$1. When HSC cells transdifferentiating to MFB, PDGF-C mRNA was strongly induced: PDGF-C up to 5 fold from day 2 to day 8. This research demonstrates that PDGF-C may fulfill specific functions in hepatic fibrogenesis (Breitkopf et. al, Cytokine 31, 349 (2005)).

PDGF-C is a multi-domain protein (345 amino acids), consisting an N-terminal domain (residue 46-163), which is homologous to the CUB domain of neuropilin-1, NP-1, and a C-terminal domain (residue 235-245, GFD, growth factor domain), which has 23% homology with other PDGF members. These two domains can be separated by protease digestion in blood. PDGF-C can directly bind to PDGFR-$\alpha$ and PDGFR-$\beta$. According to competition assays and immunogenic precipitation experiments, PDGF-CC (PDGF-C homodimer) binds well with PDGFR-$\alpha$ and PDGFR-$\beta$. (Gilbertson et. al. JBC 276(29), 27406 (2001)). In addition, PDGF-CC strongly activate the tyrosine phosphorylation of PDGFR-$\alpha$ and PDGFR-$\beta$. GFD domain of PDGF-CC can bind well to PDGFR $\alpha/\alpha$ or PDGFR $\beta/\beta$ homodimer, and PDGFR $\alpha/\beta$ heterodimer.

Kidney fibrosis is the end result of pathological changes of renal tubes and intercellular substance. Kidney fibrosis is the general path for all kidney diseases and late stage kidney failure. The pathological characteristics are ECM deposition and loss of glomerular cells. The initiation and development of kidney disease are complex, which involve many factors, such as PDGF, TGF-$\beta$, and connective tissue growth factor (CTGF), and etc. PDGF affects kidney disease by inducing mesangial cell proliferation and renal tube and intercellular substance fibrosis. In normal rats, PDGF-AA is situated at renal papillary area, which affects cell migration; PDGF-BB is weakly expressed in renal tube and intercellular substance, which induces DNA synthesis and mitosis; PDGF-CC is expressed in glomerular endothelial cells, glomerular endothelial cells, vascular smooth muscle cells, glomerular capillary endothelial cells. When mesangial cells, kidney epithelial cells, and interstitial cells are damaged, PDGF-CC expression is increased. PSGF-CC's ability to activate mitosis is stronger than PDGF-AA, but weaker than PDGF-BB.

During chronic kidney inflammation process, stromal fibroblast cells proliferate, and its activated form is Myofibroblast (MyoF). MyoF can express α-smooth muscle actin (α-SMA), participating in tubulointerstitial fibrosis. Injecting PDGF-AA or PDGF-BB into mouse tubulointerstitial matter continuously for 7 days, PDGF-AA does not have any effect, but PDGF-BB induces tubulointerstitial fibrosis in a dose dependent manner. Li et al. discovered that PDGF-CC is the reason for fibroblast cells proliferation. Research data demonstrates that PDGF-CC abnormal expression is linked to tubulointerstitial fibrosis.

In anti-Thy1.1 nephritis mouse, PDGFR tyrosine kinase inhibitor significantly decreased mesangial cells proliferation, activated mesangial cells amount and Type IV collagen deposition. The mechanism is that STI571 inhibits ATP binding to Tyrosine kinase, so that phosphorylation and signal transduction are inhibited. The above data demonstrated that inhibitors to PDGFR pathway can significantly ease glomerulosclerosis.

Under pathological condition, PDGF expression increases. Overexpressed PDGF causes tubulointerstitial renal cell transfomation, inflammatory cell infiltration, and cytokine production, which leads to tubulointerstitial fibrosis and malignant renal diseases. Decrease or inhibition of PDGF synthesis or activity has certain effect on treating kidney fibrosis.

PDGF-B or PDGF-D injection or overexpression induces vascular mesangial proliferation and kidney fibrosis. Interference experiment demonstrated that PDGF-C induces tubulointerstitial fibrosis. PDGF-B and -D are key factors for vascular mesangial proliferation and kidney fibrosis. Thus PDGF family is growth factor for kidney diseases, and strongly stimulate the proliferation of mesangial cells.

Currently, this field is in need of an effective product to prevent and treat fibrosis diseases, such as liver fibrosis, kidney fibrosis, and lung fibrosis.

2) Cancer

Dimerization and autophosphorylation of PDGFR occur upon receptor-ligand interaction. Phosphorylated tyrosine residues, in the context of specific amino acid residues, interact with Src homology 2 domains (SH2) of intracellular signaling molecules. These include phospholipase γ (PLC-γ), Ras GTPase-activating protein (Ras-GAP), p85 subunit of PI3K, growth factor receptor-bound protein 2 (Grb 2), Syp (tyrosine-specific phosphatase), Src homology and collagen protein (Shc), and Src. These signaling molecules further transduce signal transduction pathways by activating downstream signaling molecules such as mitogen activated protein kinase family members (ERKs, JNKs), and focal adhesion kinase (FAK, a mediator of integrin signaling pathway) among others. These signals enter the nucleus and stimulate expression of a set of immediate-early-response genes that mediate PDGF-induced cellular processes including cell cycle, cell migration, and transformation.

Studies during the past two decades clearly indicate the significance of PDGF in human tumors. In vitro, overexpression of the v-sis oncogene product (p28v-sis) or PDGF-B in cells that express these receptors enhances transformation, indicating autocrine mechanism in tumorigenesis. Recent studies revealed a critical role for paracrine PDGF signaling in carcinogenesis through the regulation of epithelial-stromal interactions. Using nude mice, it was demonstrated that PDGF activation of stromal cells results in tumorigenic conversion of immortal human keratinocytes. Enhanced PDGF immunostaining was detected in soft tissue tumors and advanced breast tumors.

The fatal phenotypes of PDGF- or PDGFR-deficient mice include cardiovascular and hematological defects. PDGFs produced by endothelial cells in vessels promote recruitment and proliferation of vascular smooth muscle cells/pericyte progenitors expressing PDGFR. Chemotactic and mitogenic activities mediated by the PDGF/PDGFR paracrine signaling loop are crucial for the formation, branching, and maintenance of blood vessels. As in embryogenesis, PDGF plays a critical role for angiogenesis in human tumors. Tumor angiogenesis, required for tumor outgrowth and metastasis, is a complex and highly regulated process involving many different cell types and extracellular factors. PDGF is also involved in angiogenesis and tumor metastasis. Thus inhibiting PDGF signaling pathway could potentially attenuate primary and metastatic. (Yu et al., J of Biochem and Mol Bio, 36(1), 49 (2003)).

SUMMARY OF THE INVENTION

The aim of this invention is to provide the composition of a peptide or its fragment or its homologous peptide, or its derivatives with activity to bind the extracellular domain of PDGFR-α, or -β, but does not dimerize by itself, and their usage to prevent and treat fibrosis diseases and cancer (primary and metastatic) in human and animal.

The inventors of this patent discovered a series of peptide sequences, which include peptide sequence which is a fragment in the GFD domain of PDGF-C (C-terminal of PDGF-C), and a series of peptides which have certain amino acid alterations using peptide sequences in the GFD domain of PDGF-C as bases. These peptides have three-dimensional structure, which allow them to bind to PDGFR-α, or -β, but do not have the activity of PDGF family members (cannot dimerize). Thus they block PDGF family and PDGFR binding and inhibit downstream signaling transduction pathways to realize its function to prevent and treat fibrosis diseases and cancer (primary and metastatic) in human and animal.

This invention provides a peptide, or its mutant, or other active derivatives with the same 3-D structure. The peptide according to the present invention includes SEQ ID NO: 1 sequence.

In one embodiment according to the present invention, the peptide is selected from the group consisting of:
 (i) SEQ ID NO: 2 sequence;
 (ii) SEQ ID NO: 2 sequence, any cysteine residue changed to serine residue;
 (iii) SEQ ID NO:3 sequence; or
 (vi) SEQ ID NO: 3 sequence, any cysteine residue changed to serine residue.

In one embodiment according to the present invention, the above peptide is obtained from recombinant source, purified from natural source, or from chemical synthesis.

The present invention further provides nucleotide sequence which encodes the peptides according to the present invention.

The present invention also provides a use of the peptide according to the present invention in preparation of medicine for prevention or treatment of human or animal tissue fibrosis and cancer.

In one embodiment according to the present invention, the tissue comprises liver, kidney, or lung in human and animal.

In one embodiment according to the present invention, the cancer comprises primary and metastatic cancers in human and animal.

The present invention also provides a pharmaceutical composition for prevention and treatment of human or animal tissue fibrosis and cancers, comprising the peptide according to the present invention and a pharmaceutically acceptable carrier such as BSA, PEG, albumin.

In one embodiment according to the present invention, the pharmaceutical composition further comprises other chemotherapy drugs, including, but not limited to Gleevec.

In one embodiment according to the present invention, the pharmaceutical composition is in the form of oral dosage, subcutaneous injection dosage, intradermal injection dosage, intramuscular injection dosage, intravenous injection dosage and any other dosage, such as nasal dosage.

DETAILED DESCRIPTION

Figure 1:
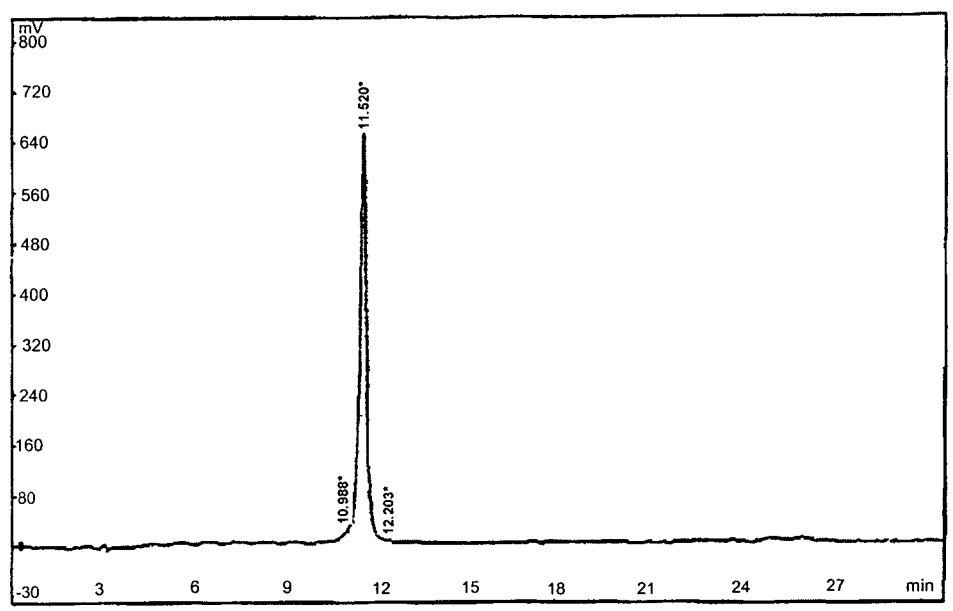
FIG. 1. HPLC graph of the peptide in example 1.

The activity domain of PDGF-C is located at the C-terminal GFD (growth factor domain, 113 amino acids). The inventors of this patent used primary sequence alignment, 2-D and 3-D structure computer simulation to design a series of peptide sequences. These peptides have the characteristics of not forming dimer, but still binding to extracellular domain of PDGFR, so they block PDGF and PDGFR signaling transduction pathways to prevent and treat fibrosis diseases and cancer (primary and metastatic).

This patent provides a peptide, which includes SEQ ID NO:1 sequence.

The peptides from this invention can be recombinant, natural, or synthetic. In detail, the peptides can be purified from natural sources, or from chemical synthesis, or from recombinant source from prokaryote or eukaryote sources (for example, bacteria, yeast, plant, insects, or mammalian cells).

This patent provides the amino acid sequence of SEQ ID NO: 1 peptide. It also provides peptide sequences which have the same function like SEQ ID NO: 1 (not forming dimmer, but still binding to extracellular domain of PDGFR). These mutant peptides include, but not limited to: one or more (1-20, 1-10, 1-5, or 1-3) amino acid deletion, insertion and or replacement and addition of one or more (within 20, within 10, or within 5) amino acids at the N-terminal and/or C-terminal of the peptides, conservative mutation of the sequence. For example, in this field, amino acid mutation with similar activity amino acids (hydrophobic residue replaced with hydrophobic residue, acidic residue replaced with acidic residue, or basic residue replaced with basic residue) will not change the function of the peptide. Addition of one or more residues at the N-terminal and/or C-terminal of the peptide normally will not change the characteristics of the peptide. The claimed peptide sequences also include active derivatives of SEQ ID NO: 1 peptide.

In the examples of this patent, peptide sequences are selected from and include the following peptides:
  (i) SEQ ID NO: 2 sequence;
  (ii) SEQ ID NO: 2 sequence, any cysteine residue changed to serine residue;
  (iii) SEQ ID NO:3 sequence; or
  (vi) SEQ ID NO: 3 sequence, any cysteine residue changed to serine residue.

This patent additionally provides the usage of these peptides to prevent and treat fibrosis diseases and cancer (primary and metastatic) in human and animal.

This patent provides the formulation of the peptides with suitable pharmaceutical conjugations, such as BSA, PEG, albumin to increase its half-life and other activities. These new peptide conjugates will be used to prevent and treat fibrosis diseases and cancer (primary and metastatic) in human and animal.

In addition, this patent provides a formulation, including (a) safe and pharmaceutically effective dose of peptides in this patent, with conjugate, or other combination; and (b) a pharmaceutically acceptable carrier. The dose of the above peptides is normally 10 microgram to 100 milligram per dose, or within 100 microgram to 50 milligram per dose, or 1000 microgram to 10 milligram per dose, or 3000 microgram to 5000 microgram per dose.

In one embodiment, "effective dose" in this invention denotes the dose to treat, ease, or prevent targeted disease or condition, or dose that shows treatment or prevention effect. The exact effective dose for any subject will be determined according to the subject's body type, health condition, disease characteristics, and accompanying treatment combination. Thus, the accurate dose cannot be determined beforehand. For specific situation, the physician will decide on the final effective dose for a particular subject using suitable experiments and calculations.

For the purpose of the patent, the effective dose of the above peptides for each subject is around 1 microgram to 100 milligram per kg per day, or 100 microgram to 50 milligram per kg per day. In addition, the above peptide can be in combination therapy with other chemotherapy agents, including, but not limited to Gleevec.

Pharmaceutical composition also comprises pharmaceutically acceptable carriers. "pharmaceutically acceptable carriers" do not by themselves induce any unsafe antibody, or induce excess toxicity in test subject. These carriers are well-known to technical people familiar with the art. In Remington's Pharmaceutical Sciences (Mark Pub. Co., N.J. 1991), these carriers were discussed extensively. These carriers include, but not limited to saline, buffer, glucose, water, glycerol, ethanol, adjuvant, and other combinations.

Pharmaceutically acceptable carriers in the formulation include liquid, for example, water, saline, glycerol, and ethanol. In addition, these carriers can serve the following functions, such as surfactant, emulsifier, or pH buffer.

Normally, the formulation could be injection, for example, liquid dose, or solid dose with liquid carriers added before use.

When the above peptides are in optimum formulation, they can be given to test subject for the treatment and prevention of fibrosis disease and cancer. The test subjects could be human and animals.

In this patent, the delivery method is oral, subcutaneous injection, intradermal injection, intramuscular injection, intravenous injection and other delivery methods, such as nasal. The dosing scheme could be single dose or multiple doses.

Below we explain more in detail the patent using examples. These examples only helps to explain this patent, but are not limited to this patent. If no experimental protocols are included, the experiments were conducted according to manufacturer instructions under normal conditions.

EXAMPLES

Example 1

SEQ ID NO: 1 Sequence Solid-Phase Synthesis (Manual)

Raw material and research reagents:
Amino Acids Raw Material
Fmoc-L-Ala-OH, Fmoc-L-Arg(Pbf)-OH, Fmoc-L-Asn (Trt)-OH, Fmoc-L-Asp(OtBu)-OH, Fmoc-L-Cys(Trt)-OH, Fmoc-L-Glu(OtBu)-OH, Fmoc-L-Gln(Trt)-OH, Fmoc-L-Gly-OH, Fmoc-L-Ile-OH, Fmoc-L-Leu-OH, Fmoc-L-Lys (Boc)-OH, Fmoc-L-Met-OH, Fmoc-L-Phe-OH, Fmoc-L-Pro-OH, Fmoc-L-Ser (tBu)-OH, Fmoc-L-Thr(tBu)-OH, Fmoc-L-Trp(Boc)-OH, Fmoc-L-Tyr (tBu)-OH, Fmoc-His (Trt)-OH, Fmoc-L-Val-OH (Suzhou Tian-ma Medical Group, Final chemical Co., Ltd.)

Research Reagents: HBTU (Suzhou Tian-ma Medical Group, Final chemical Co., Ltd.), HOBT (Suzhou Tian-ma Medical Group, Final chemical Co., Ltd.), DIEA (Sinopharm, Shanghai Chemical Reagents Co.)

Solvent: DMF (Dikma), DCM (Dikma), Acetonitrile (Fisher)

Resin: 2-Chlorotrityl Chloride Resin (Tianjin Nankai Synthesis Technology Co., Ltd.)

Piperidine (Sinopharm, Shanghai Chemical Reagents Co.)
TFA (J.T.Baker), TIS (ALDRICH), EDT, TIS (ALDRICH)
Nitrogen (Shanghai Biou Gas Industrial Co.)
Anhydrous Ethyl Ether (Shanghai Shiyi Chemical Reagent Co., Ltd)
Analytical Balance (Beijing Saiduoli Balance Co. Ltd.)
Equipment:
SYMPHONY, 12 channel peptide synthesizer (Type: SYMPHONY, Software: Version.201. Manufacturer: Protein Technologies Inc)
SHIMADZU HPLC (Software: Class-VP. Serial System, Manufacturer: SHIMADZU)
LABCONCO Lypholize (Type: Freezone. Plus. 6, Manufacturer: LABCONCO,
Centrifuge (Shanghai Anting Scientific Equipment Co., Type: TDL-40B)
SEQ ID NO: 1 Sequence Solid-Phase Synthesis (Manual)

1) Resin Swelling
Add 2-Chlorotrityl Chloride Resin into the reaction vessel, and then add DMF (15 ml/g), shake for 30 min.

2) Coupling the first amino acid
Filter the solvent via the sand filter. Add 3-fold moles excess of Fmoc-L-Gly-OH, and DMF to the reaction vessel. Dissolve in DMF and shake for 30 min 3) Deprotection
Get rid of DMF, add 20% piperidine-DMF solution (15 ml/g), stand for 5 min and get rid of the solvent. Then add 20% piperidine-DMF solution (15 ml/g) again, stand for 15 min.

4) Monitoring
Get rid of piperidine solvent, transfer some resin beads to a tube. Wash 3 times with ethanol, then add a drop of ninhydrin, a drop of KCN and a drop of Phenol solution. Heat at 105 C-110C. The color turned deep blue (a positive reaction).

5) Wash
Wash with DMF (10 ml/g) twice, methanol twice, and DMF (10 ml/g) twice.

6) Condensation
Method a: Dissolve 3-fold mole excess protected amino acid (FOMC-Asp-OH) and HBTU in DMF. Add the solution to the reaction vessel, and add 10-fold mole excess NMM immediately. React for 30 min.

Method b: Dissolve 3-fold mole excess protected amino acid (FOMC-Asp-OH) and HOBT in DMF. Add the solution to the reaction vessel, and add 3-fold mole excess DIC immediately. React for 30 min.

7) Wash
Wash with DMF (10 ml/g) once, methanol (10 ml/g) twice, and DMF (10 ml/g) twice.

8) Repeat
Repeat Step 2 to Step 7 for each of the subsequent amino acid according to SEQ ID NO: 1 sequence 9) Last amino acid
The method to wash resin after the last amino acid coupling and deprotection is as below:
Wath with the following reagents: DMF (10 ml/g) twice, methanol (10 ml/g) twice, DMF (10 ml/g) twice, DCM (10 ml/g) twice. And then remove the solvent and dry the resin by vacuum filtration for 10 min.

10) Cleavage of the peptide from resin
Cleavage reagent: TFA 94.5%; $H_2O$ 2.5%; EDT 2.5%; TIS 1%
Cleavage time: 2 hours.

11) Drying and Washing
Blow-dry the cleavage solution above with Nitrogen, then wash with ether 6 times. Air dry the crude peptide at room temperature.

12) Purification of the crude product by HPLC
Dissolve the crude peptide with water or small amount of acetonitrile. The crude peptide is purified according to the following steps:
Pump A: 0.1% trifluoroacetic in 100% water
Pump B: 0.1% trifluoroacetic in 100% acetonitrile
Total Flow rate: 1.0 ml/min
Volume: 30 ul
wavelength: 220 nm
Gradient:

| Time (minutes) | A | B |
|---|---|---|
| 05.00 | 90% | 10% |
| 30.00 | 20% | 80% |
| 30.10 | | stop |

<Detector A>
Column: Venusi MRC-ODS C18 30×250 mm

13) Freeze dry the solution after the purification, which is the final product.

Figure 2:
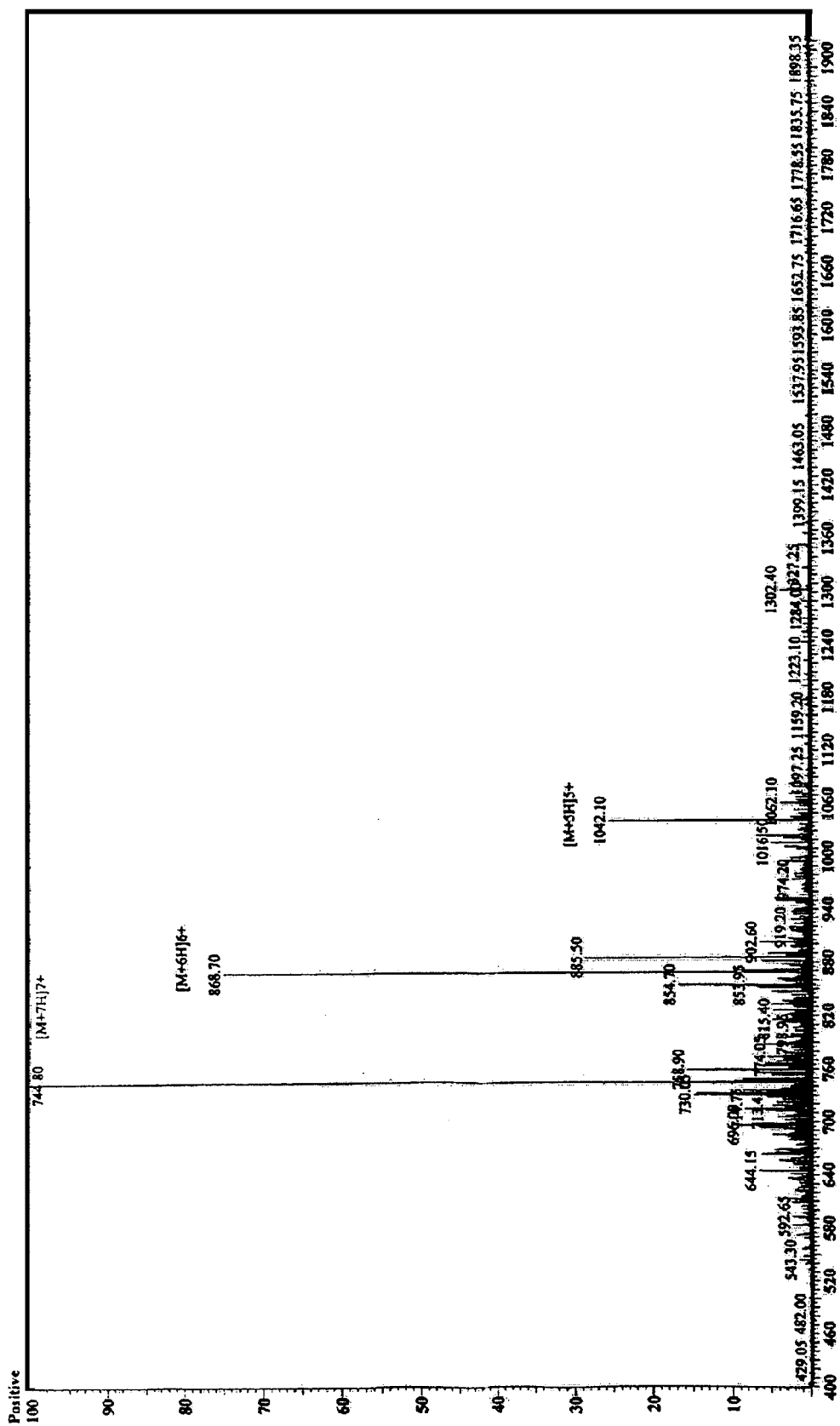
FIG. 2. Mass spectrometry graph of the peptide in example 1.
Figures 3, 4:
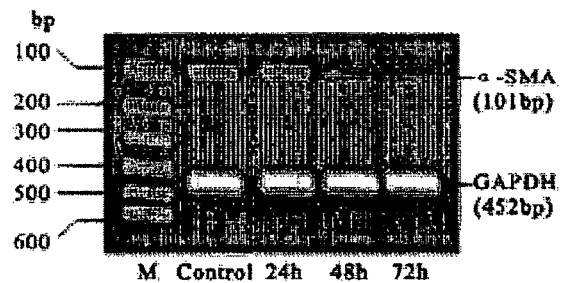
FIG. 3. Sequencing result of the peptide in example 1.
FIG. 4. Electrophoresis graph of the expression inhibition of the peptide in example 1 towards HSC α-SMA mRNA FIG. 5. Electrophoresis graph of the protein expression inhibition of the peptide in example 1 towards α-SMA protein FIG. 6. The peptide in example 1 can inhibit tumor cells attachment to base membrane FIG. 7. The peptide in example 1 can inhibit migration ability of tumor cells through base membrane FIG. 8 Inhibitory activities in PDGFR intracellular Ras-Raf signaling pathway of the peptide in example 1.

14) Verification
The final product was examined using HPLC for purity (97.1%, FIG. 1). Its molecular weight was examined using mass spectrometry. Theoretical molecular weight is 5203.98, and actual molecular weight is 5206.1 (FIG. 2). The sequence of the final product was confirmed by the Proteomics Analytical Center from Shanghai Life Science Research Institute at China Academy of Sciences (FIG. 3).

15) Storage

The white powder was sealed and stored at −20 C.

Example 2

SEQ ID NO: 1 Peptide Synthesis Using Automatic Peptide Synthesizer (Symphony Synthesizer)

Protocol:

1) Use software to calculate needed amount of protected amino acid solution, condensation reagent, and cleavage reagent. Add adequate amount of DMF and DCM in their corresponding bottles in the machine.

2) Add 100 umol FMOC-L-Gly-2-Chlorotrityl Chloride Resin in the reaction vessel. Place 15 mg centrifuge tube in the conduit to collect the cleavage solution.

3) Edit the program: generally the time for resin swelling is 30 min, deprotection time is 5 min and 15 min (twice), condensation time is 30 min, and cleavage time is 2 hour.

4) Switch on the machine and run the program.

5) Finally, precipitate the cleavage solution with ether, and then centrifuge and blow dry, and purify the crude peptide by HPLC. The final product was examined using HPLC for purity (97.1%, FIG. 1). Its molecular weight (SEQ ID NO: 1) was examined using mass spectrometry. Theoretical molecular weight is 5203.98, and actual molecular weight is 5206.1 (FIG. 2). The sequence of the final product was confirmed by the Proteomics Analytical Center from Shanghai Life Science Research Institute at China Academy of Sciences (FIG. 3).

Example 3

Effect of Peptide Seq. No. 1 on Liver HSC Cell Amount and Activation

Material and Methods:

1. Five Male SD rat, weight (250±25) g, DMEM culture, Pancreatin (including EDTA), Lipofectamine 2000, Trizol, serum from newborn calf (Invitrogen), Proteinase E (pronase), collagenase B, and DNA Enzyme (Roche), Nycodenz (Sigma), Antibody p-FAK Tyr397, Desmin and α-smooth muscle actin (α-SMA), monoclonal antibody (Santa Cruz Co.).

RT-PCR kit (MBI).

2. Culture HSC

HSC from SD rats were separated using centrifuging on gradient created by Pronase-collagenase and Nycodenz. HSC cells at $1.5 \times 10^5/cm2$ was plated at 6-well plate, or culture dish (100 mm diameter). The culture medium is DMEM with 20% serum from newborn calf. The purity of HSC cells was determined using Vitamin A self-fluorescence and anti-Desmin immunocytochemistry experiments. Cell viability was determined using trypan blue staining. First generation HSC's purity and viability were 90% and 95% respectively. HSC can self-activate if grown in non-ECM condition, which means HSC can express α-SMA, and Vitamin A drop disappears. After cell fusion, activated HSC is released with trypsin, and propagate.

3. MTT Assay

Peptide SEQ ID NO: 1, (1 μM), 24 hour, 48 hour, or 72 hour. Use MTT assay to examine the proliferation of HSC cells.

4. RT-PCR examination to check α-SMA mRNA expression

Use Trizol reagent to extract total RNA, then conduct two-step RT-PCR according to kit instructions.

```
α-SMA upstream primer:
5' - AAGAGGAAGACA GCA CAG C TC-3';

Downstream primer:
5' - GATGGATGGGAAAACAGC C-3',

Final product:
101 bP α-SMA cDNA fragment.

GAPDH upstream primer:
5' - ACCACAGTCCATGCCATC AC-3',

Downstream primer:
5' - TCCACCACCCTGTTGCTGTA-3',

Final product:
452 bp GAPDH cDNA fragment.
```

5. Western blot to examine α-SMA protein expression

Collect cells and add cell lysis buffer, extract total protein. Total protein amount was determined using Bradford assay. 40 μg total protein was examined using 10% SDS polyacrylamide gel. The gel was probed using monoclonal antibody against α-SMA.

6. Statistical calculation

The result is expressed using x±s, SPSS 10. 0 software, $P<0.05$.

Result

1. Effect of Peptide SEQ ID NO:1 on Proliferation of HSC Cells.

After 24 hours, the inhibition rate of peptide SEQ ID NO:1 at 1 μM is 45.5%±5.8%. After 48 or 72 hours, the inhibition rate of peptide SEQ ID NO:1 at 1 μM is 61.8%±4.3% and 85.6%±5.8, respectively.

2. Effect of Peptide SEQ ID NO:1 on Expression of α-SMA mRNA

Different from resting state HSC, α-SMA mRNA expression is one important characteristics of activated HSC. According to RT-PCR experiment, peptide SEQ ID NO:1 inhibits α-SMA mRNA expression after 48 hours (FIG. 4).

3. Effect of Peptide SEQ ID NO:1 on α-SMA Protein Expression

Figure 5:
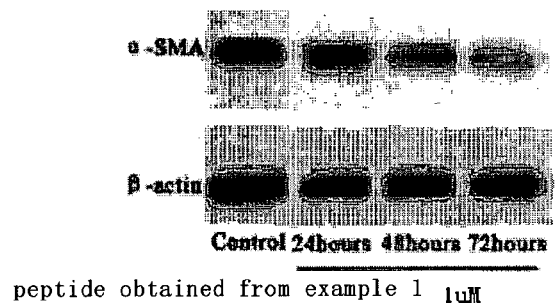

According to Western Blot experiment, peptide SEQ ID NO:1 starts to decrease α-SMA protein expression after 48 hours, and significantly decrease α-SMA protein expression after 72 hours (FIG. 5).

Example 4

Efficacy Experiment of Peptide SEQ ID NO:1 in Liver Fibrosis Animal Model

To evaluate the protective effect of peptide SEQ ID NO:1 on liver damage, we used chronic liver fibrosis model (rat CC14 model) for efficacy evaluation.

Results demonstrated that peptide SEQ ID NO:1 at treatment high dose (50 μg/mg) and prevention low dose (10 μg/mg) can significantly lower liver damage parameters in rat CC14 model. In the treatment group and prevention group, SEQ ID NO:1 improved many liver parameters ($P<0.01$, $P<0.05$): treatment high dose group (total protein, albumin, serum glutamate pyruvate transaminase (SGPT), aspartate aminotransferase, alkaline phosphatase, and glucose), treatment low dose group (total protein, albumin, and glucose), prevention high dose group (total protein, albumin, SGPT, aspartate aminotransferase, and glucose), prevention low dose group (total protein, albumin, SGPT, and glucose).

Compared to control group, Hydroxyproline significantly increase in chronic CC14 liver damage rat model (P<0.05). Hydroxyproline amount was eased in various treatment group, with the best effect in treatment high dose group (P<0.05).

According to histology report, liver tissue of CC14 model group displayed structural disorder. Over 80% of liver cells showed significant steatosis, and many fat cavities in liver cells. In one case, there is epidermal hyperplasia of fibrous tissue in liver. In treatment high dose group, 2 cases showed steatosis, and fat cavities in liver cells (>80%), 2 cases showed less steatosis and fewer fat cavities in liver cells (50-60%), and 4 cases displayed even less steatosis and fewer fat cavities in liver cells (<30%). All cases in prevention low dose group showed less steatosis and fewer fat cavities in liver cells (60-80%). In prevention high dose group, 5 cases showed less steatosis and fewer fat cavities in liver cells (60-80%), and 3 cases displayed even less steatosis and fewer fat cavities in liver cells (50-60%).

In summary, peptide SEQ ID NO:1 can improve liver damage caused by CC14 in rat, and improve serum biochemical parameters, liver hydroxyproline amount, and liver pathological features.

Reagents and Methods

1) Drugs

Peptide SEQ ID NO:1 (Example 2);

Drug for injection, provided by Zhengda Tianqing.

Positive control drug, Gan-li-xin (Diammonium glycyrrhizinate) injection, 10 ml:50 mg, Jiangsu Zhengda Tianqing Pharmaceutical Co., Ltd.

2) Animal

SD rat, 180-220 g, female and male (1:1)

3) Main Reagents

CC14, Shanghai Lingfeng Chemical Reagents Co., Ltd., Lot No: 061101;

Sesame oil, fine peanut oil;

Hydroxyproline examination kit (Nanjing Jianchen Co.)

4) Main Equipments

BS210S analytical balance (0.1 mg~10 g) (German Sartorius);

752C UV-Vis spectrophotome (Shanghai No. 3 analytical equipment co.);

Centrifuge (Beijing Medical Centrifuge Co.);

Automatic Biochemical Examination Machine (OLYMPUS Au 800, Japan);

FEJ-200 analytical balance (0.1~200 g) (Fuzhou Furi Hengzhibao Electric Co. Ltd.)

5) Experiments

Rat CC14 liver damage model

Dose Group:

110 rats, weight 180-220 g, 7 groups:

(1) Control group: saline, sc, 2 ml/kg, 10 rats (2) model group: 40% CC14, sc, 2 ml/kg, 17 rats (3) Gan-li-xin group: 25 mg/kg, iv, 10 ml/kg, 15 rats (4) Prevention, high dose group: 50 µg peptide SEQ ID NO:1/kg, iv, 10 ml/kg, 17 rats (5) Prevention, low dose group: 10 µg peptide SEQ ID NO:1/kg, iv, 10 ml/kg, 17 rats (6) Treatment, high dose group: 100 µg peptide SEQ ID NO:1/kg, iv, 10 ml/kg, 17 rats (7) Treatment, high dose group: 20 µg peptide SEQ ID NO:1/kg, iv, 10 ml/kg, 17 rats Model Construction and Dosing Method Except for control group, inject 40% CC14 subcutaneously twice (Tuesday, and Friday) every week in Group (2) to (6), drug volume (0.2 ml/100 g, the first time 0.5 ml/100 g). CC14 Model construction is 6 weeks. Parallel to the model construction, inject intravenously peptide SEQ ID NO:1 at 50 µg/kg and 10 µg/kg in group (4) and (5), respectively, once a day for 6 weeks. For Group (3), (6), and (7), starting from week 5, inject Gan-li-xin 25 mg/kg, peptide SEQ ID NO:1 at 100 µg/kg and 20 µg/kg, respectively, once a day, continuously for 2 weeks.

Examination Parameters

All rats were weighed once a week during model construction and drug injection. According to weight, the dose of drugs is adjusted. 24 hours after the last time of CC14 injection, liver weight parameters were examined.

Blood was extracted from femoral artery and serum was separated. The following parameters were examined: serum alanine aminotransferase (ALT), aspartate aminotransferase (AST), Bilirubin (TB), Alkaline phosphatase (ALP), total protein (TP), albumin (ALB), globulin (G), albumin/globulin ratio (A/G), glucose (GLU), total cholesterol (TCH), triglyceride (TG).

Liver homogenate: to examine cholesterol (TCH), triglyceride (TG), alanine aminotransferase (ALT), and aspartate aminotransferase (AST).

200 g liver, dry at 110 C, examine Hydroxyproline (HPA).

Part of the liver is fixed in formalin for histology examination.

Experimental Results

1) Effect of Drugs to Rat Body Weight, Liver Weight, and Liver Parameters

Compared to control group, the liver parameters of CC14 liver damage group increase significantly (P<0.01). In various treatment group, these parameters were improved, with treatment high dose group and prevention low dose group having statistical significant differences (P<0.05) Please see below Table 1 (*vs control group, # vs CC14 model group)

TABLE 1

Effect of drugs on rat body weight, liver weight, and liver parameters

|  | Control Group | Model Group | Gan-li-xin 25 mg/kg | Treatment, High dose 100 µg/kg | Treatment, low dose 20 µg/kg | Prevention, High dose 50 µg/kg | Prevention, low dose 10 µg/kg |
|---|---|---|---|---|---|---|---|
| weight (g) | 292 ± 106.4 | 284.7 ± 50.7 | 269.2 ± 71.3 | 246.4 ± 54.2 | 289.4 ± 69.6 | 281 ± 53.7 | 276.4 ± 49.6 |
| Liver weight (g) | 10.4 ± 4.2 | 13.2 ± 3.3 | 11.6 ± 3.5 | 10.1 ± 3.2# | 12.9 ± 4.7 | 12.1 ± 2.5 | 11.3 ± 2.5 |
| Liver parameters | 3.5 ± 0.7 | 4.6 ± 0.8* | 4.4 ± 0.6 | 4.0 ± 0.5# | 4.4 ± 0.8 | 4.3 ± 0.4 | 4.1 ± 0.4# |

2) Effect of Drugs on Rat Biochemical Parameters

Compared with control group, CC14 liver damage animal model group showed increased level of serum alanine aminotransferase, aspartate aminotransferase, and alkaline phosphatase, decreased level of total protein, albumin, glucose, and triglyceride. Gan-li-xin group (12.5 mg/kg) improved the parameters above to a certain extent, showing statistical significant improvement in aspartate aminotransferase (AST) and glucose (GLU) ($P<0.05$). Peptide SEQ ID NO:1 groups (treatment and prevention groups) also improved the above parameters, with statistical significant improvement (compared with CC14 model group): Treatment high dose group (TP, ALB, ALT, AST, ALP, GLU), Treatment low dose group (TP, ALB, GLU), Prevention high dose group (TP, ALB, ALT, AST, GLU), Prevention low dose group (TP, ALB, AST, GLU). Please see table 2 for details (*vs control group, # vs CC14 model group).

(60-80%), and 3 cases displayed even less steatosis and fewer fat cavities in liver cells (50-60%).

Example 5

In Vitro Anti-Cancer Efficacy Evaluation of Peptide SEQ ID No:1

1. Equipments

Digital Water bath: HH-4 (Guohua Electric Co., Ltd)
Incubator: HERA cell 150 (Thermo Electron Corporation)
Microscope: BDS200-PH (Chongqing Aote Optic Equipment Co.)
Tabletop Centrifuge: TGL-16G (Shanghai Surgical Device Co.)
Clean bench: SW-CJ-IFD (Sujing Group Antai Co.)

TABLE 2

Effect of drugs to rat biochemical parameters

|  | Control Group | Model Group | Gan-li-xin 25 mg/kg | Treatment, High dose 100 µg/kg | Treatment, low dose 20 µg/kg | Prevention High dose 50 µg/kg | Prevention low dose 10 µg/kg |
|---|---|---|---|---|---|---|---|
| TP g/L | 73.6 ± 9.6 | 62.8 ± 3.6* | 64.8 ± 5.4 | 70.4 ± 4.4# | 69.1 ± 6.1# | 68.3 ± 4.1# | 66.4 ± 4.6# |
| ALB g/L | 22.7 ± 4.4 | 16.5 ± 2.4* | 17.9 ± 2.5 | 19.7 ± 3.7# | 18.8 ± 2.5# | 20.8 ± 2.0# | 18.8 ± 2.4# |
| Bilirubin umol/L | 3.0 ± 0.5 | 3.0 ± 0.9 | 3.3 ± 0.6 | 2.9 ± 0.4 | 3.3 ± 0.8 | 3.3 ± 0.1 | 3.3 ± 0.5 |
| ALT IU/L | 40.7 ± 5.2 | 97.6 ± 21* | 73.6 ± 25# | 69.8 ± 31.3# | 90.9 ± 37.3 | 75 ± 29.4# | 80.6 ± 21.3# |
| AST IU/L | 186.6 ± 37.3 | 273.9 ± 48.6* | 253.3 ± 69.3 | 219.6 ± 56.7# | 260.0 ± 73.1 | 236.8 ± 27.2# | 248.8 ± 38.3 |
| ALP IU/L | 195.0 ± 90.7 | 354.3 ± 159.0* | 351.6 ± 134.1 | 216.5 ± 91.0# | 357.1 ± 120.7 | 266.3 ± 85.7 | 304.3 ± 90.4 |
| GLU mmol/L | 5.7 ± 0.9 | 4.7 ± 0.5* | 5.4 ± 0.7# | 6.3 ± 1.0# | 6.1 ± 0.9# | 6.5 ± 0.9# | 6.2 ± 0.7# |
| TG mmol/L | 1.5 ± 0.3 | 0.5 ± 0.2* | 0.7 ± 0.3 | 0.5 ± 0.2 | 0.5 ± 0.2 | 0.6 ± 0.1 | 0.6 ± 0.2 |
| TCH mmol/L | 2.1 ± 0.7 | 1.5 ± 0.6 | 1.7 ± 0.5 | 2.1 ± 0.8 | 1.6 ± 0.5 | 1.9 ± 0.3 | 1.6 ± 0.3 |

3) Effect of Drugs on Hydroxyproline Amount in Rat Liver

Compared with the control group, the amount of hydroxyproline increased significantly in CC14 damaged liver model group ($P<0.05$). In each treatment group, the amount of hydroxyproline is decreased, with that in treatment high dose group with statistical significant difference ($P<0.05$). Please see table 3 (*vs control group, # vs CC14 model group)

Vortex: XW-80A (Shanghai Medical University Equipment Co.)
Inverted phase contrast microscope: XSZ-D2 (Chongqing Optic Equipment Co.)
Microplate reader: Model-550 (Bio-Rad)
Balance: HC-TP-12 (Tianjin Balance Equipment Co., Ltd)

TABLE 3

Effect of drugs on Hydroxyproline amount in rat liver

|  | Control Group | Model Group | Gan-li-xin 25 mg/kg | Treatment, High dose 100 µg/kg | Treatment, low dose 20 µg/kg | Prevention High dose 50 µg/kg | Prevention low dose 10 µg/kg |
|---|---|---|---|---|---|---|---|
| hydroxy-proline ug/mg wet weight | 0.171 ± 0.015 | 0.222 ± 0.048* | 0.191 ± 0.038 | 0.165 ± 0.038# | 0.222 ± 0.048 | 0.216 ± 0.062 | 0.192 ± 0.045 |

4) Histology Examination

Control group showed ordered structure. Liver tissue of CC14 model group displayed structural disorder. Over 80% of liver cells showed significant steatosis, and many fat cavities in liver cells. In one case, there is epidermal hyperplasia of fibrous tissue in liver. In treatment high dose group, 2 cases showed steatosis, and fat cavities in liver cells (>80%), 2 cases showed less steatosis and fewer fat cavities in liver cells (50-60%), and 4 cases displayed even less steatosis and fewer fat cavities in liver cells (<30%). All cases in prevention low dose group showed less steatosis and fewer fat cavities in liver cells (60-80%). In prevention high dose group, 5 cases showed less steatosis and fewer fat cavities in liver cells 2. Cell Lines Human liver cancer cell line (SMMC-7721, BEL-7402, BEL-7402) were purchased from National Medical Academy of Sciences Tissue Bank and Chinese Academy of Sciences, Shanghai Cell line Research Institute.

3. Cell Culture

All cell lines were incubated at 37C, 5% CO2 incubator with saturated humidity. Culture media was RPMI1640 media with 10% heat inactivated FBS, penicillin 100 u/ml, streptomycin 100 u/ml. After 48 hours media was changed. Cells were released with 0.25% trypsin and propagate. Cells used in the experiment were in log phase. Cell viability was determined using trypan blue staining.

4. Methods

Take cells at log phase and release with 0.125% trypsin+ 0.01% EDTA and dilute cells to 2-4×10⁴ cells/ml. Cells were placed in 96 well plate (180 ul/well), and were incubated at 37 C CO2 incubator for 24 hours. Media was changed, then peptide SEQ ID No:1 was added to the well (20 ul/well), incubate for 72 hours. Add MTT into 96 well plate (20 ul/well), and incubate for 4 hours. Media was removed, add DMSO (150 ul/well). The plate was shaken for 10 minutes. 7 concentration points (0.1 to 10 uM) was examined. Absorbance at 570 nM was measured for each well to calculate the IC50.

IC50=(O.D. at well with no peptide−O.D. at well with peptide)/O.D. at well with no peptide 5. Results Peptide SEQ ID No:1 from Example 1 significantly inhibited human liver cancer cell growth, with IC50 at 1.25, 1.78, and 2.33 uM in SMMC-7721, BEL-7402, and BEL-7404, respectively.

Example 6

In Vivo Anti-Cancer Efficacy Experiments

Experimental animals: Female BALB/cA nude mice, age 35-40 days, weight 18-22 g, provided by Shanghai Silaike Experimental Animal Co. Ltd., certificate number: SOCK (Shanghai) 2007-0005.

The tumor of xenograft nude mice grew to 100~300 mm³. Tumor mice were divided into different groups for drug testing. In the experiment below, there were 12 nude mice in negative control group, and 6 nude mice in the group with tested drug. Tumor diameter was measured three times each week, and mice weight was measured at the same time.

T/C (relative tumor inhibition rate) % was calculated as below:

(1) tumor volume, TV, calculated as below:

$$TV = \frac{1}{2} \times a \times b^2$$

A and b are length and width.

(2) relative tumor volume, RTV, calculated as below:

$$RTV = TV_t / TV_0.$$

$TV_0$ ※ is tumor volume at the beginning of drug use ($d_0$), $TV_t$ is tumor volume at later time point.

(3) relative tumor inhibition rate T/C (%), calculate as below:

$$T/C\ (\%) = \frac{T_{RTV}}{C_{RTV}} \times 100$$

$T_{RTV}$: treatment group RTV; $C_{RTV}$: negative control RTV

1) Liver Cancer

Peptide SEQ ID No:1 from example 1 and 2 inhibits xenograph liver cancer nude mice model (H22) at 1 mg/kg, with inhibition rate of 67.8%, close to positive control Taxol's inhibition rate (10 mg/kg). At 1 mg/kg, Peptide SEQ ID No:1 from example 1 inhibits xenograph liver cancer nude mice model (BEL-7402) at 39.7%.

Peptide SEQ ID No:1 was given through tail vein (IV), at dosing of 0.5 mg/kg, 0.25 mg/kg, 0.125 mg/kg and 0.0625 mg/kg, 6 times a week. Docetaxol was positive control, at dosing of 20 mg/kg, once a week. Negative control was given saline solution. The xenograph nude mice were treated for 3 weeks.

T/C(%) for Peptide SEQ ID No:1 at 0.5 mg/kg, 0.25 mg/kg, 0.125 mg/kgin human liver cancer BEL-7402 nude mice was 64.90, 69.06, and 62.10, respectively. The best T/C (%) was 58.56% at 0.0625 mg/kg dosing. Thus Peptide SEQ ID No:1 can inhibit liver cancer growth in vivo.

2) Stomach Cancer

Peptide SEQ ID No:1 was given through tail vain (IV), at dosing of 1 mg/kg, 0.5 mg/kg, 0.25 mg/kg, 0.125 mg/kg, and 0.0625 mg/kg, 6 times a week. 5-FU was positive control, at dosing of 25 mg/kg, once a week. Negative control was given saline solution. The xenograph nude mice were treated for 3 weeks.

T/C(%) for Peptide SEQ ID No:1 at 0.125 mg/kg in human stomach cancer SGC-7901 nude mice was 47.66%. T/C(%) for 5-FU was 68.71%. Thus Peptide SEQ ID No:1 can strongly inhibit stomach cancer growth in vivo.

3) Breast Cancer

Peptide SEQ ID No:1 was given through tail vein (IV), at dosing of 2 mg/kg, 1 mg/kg, 0.5 mg/kg, 6 times a week. Docetaxol was positive control, at dosing of 20 mg/kg, once a week. Negative control was given saline solution. The xenograph nude mice were treated for 4 weeks.

T/C(%) for Peptide SEQ ID No:1 at 0.5 mg/kg in human breast cancer MDA-MB-435 nude mice was 49.40%. T/C(%) for docetaxel was 16.51%. Thus Peptide SEQ ID No:1 can strongly inhibit breast cancer growth in vivo.

4) Lung Cancer

Peptide SEQ ID No:1 was given through tail vein (IV), at dosing of 0.5 mg/kg, 0.25 mg/kg, and 0.125 mg/kg, 6 times a week. Docetaxol was positive control, at dosing of 20 mg/kg, once a week. Negative control was given saline solution. The xenograph nude mice were treated for 3 weeks.

T/C(%) for Peptide SEQ ID No:1 at 0.25 mg/kg, 0.125 mg/kg in human lung cancer A549 nude mice was 47.98 and 48.96%, respectively. T/C(%) for docetaxel was 18.60%. Thus Peptide SEQ ID No:1 can strongly inhibit lung cancer growth in vivo.

In all the xenograph tumor mice models, the weight of the mice was not affected by Peptide SEQ ID No:1 at different concentration, which demonstrated the safety profile of Peptide SEQ ID No:1. But the weight of mice from positive control chemotherapy drugs was greatly affected.

Example 7

Inhibition of Migration Ability of Liver Cancer Cells

Peptide SEQ ID No:1 from example 1 can inhibit human liver cancer cell BEL-7402 migration from base membrane, at 0.01, 0.1, or 1 mg/ml (12 hour incubation).

Figure 6:
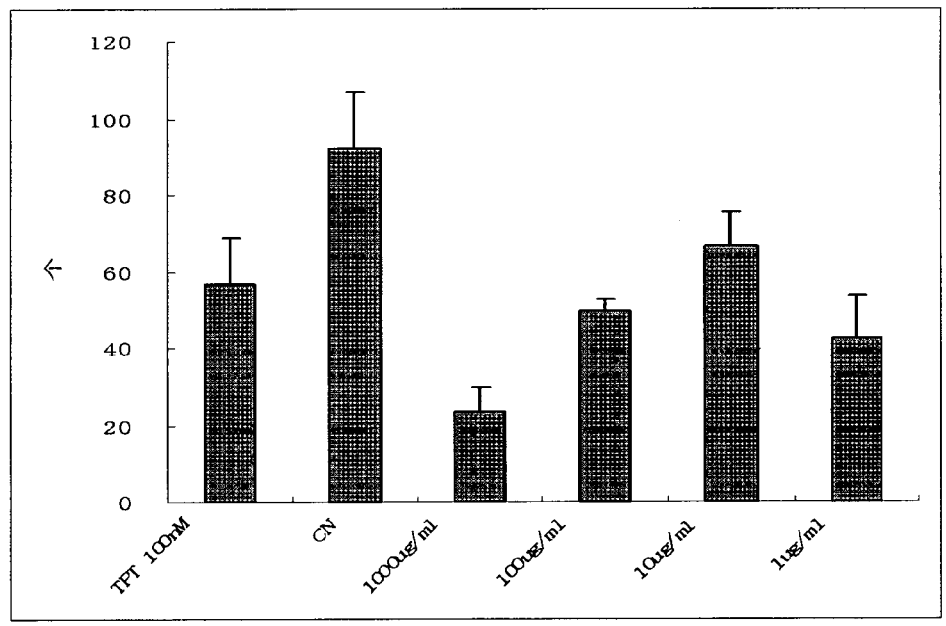
Figure 7:
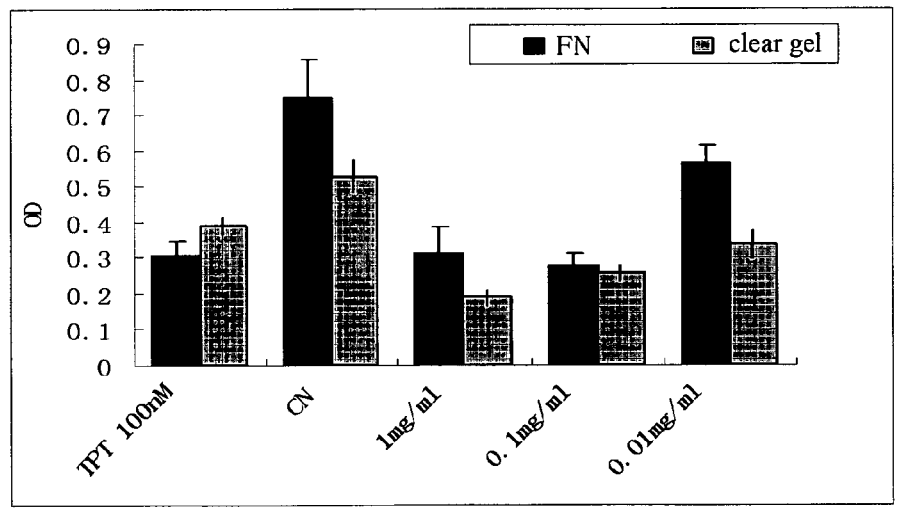
Figure 8:
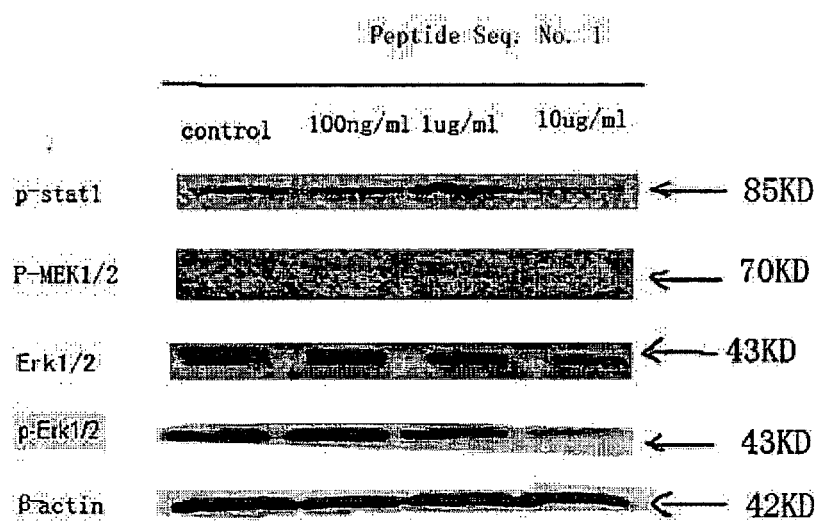
Figure 9:
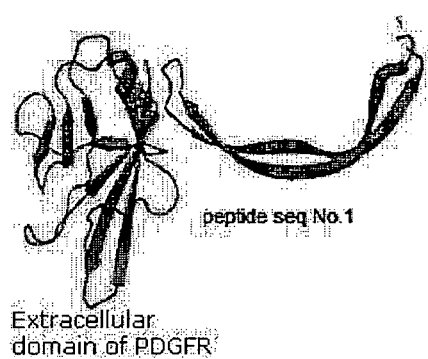
FIG. 9 Simulated 3-D structure of the peptide in example 1 and its binding to the extracellular domain of PDGFR.

FIG. 6 showed that Peptide SEQ ID No:1 inhibited cancer cell attachment to base membrane after peptide was incubated with cancer cells for 12 hours. FIG. 7 showed that Peptide SEQ ID No:1 inhibits cancer cell migration ability through base membrane after peptide was incubated with cancer cells for 12 hours Example 8

Inhibitory effect of Peptide SEQ ID No:1 on PDGFR Intracellular Ras-Raf Signaling Pathway Various concentration of Peptide SEQ ID No:1 was incubated with Human Umbilical Vein Endothelial Cells (HUVEC) cells for 6 hours. Protein was extracted from these cells and western blot was performed. Antibody for p-stat1: Antibody against phophorylated-Tyr701; Antibody for p-MEK1/2: Antibody against phophorylated-Ser217/221 peptide;

Antibody for p-Erk1/2: Antibody against phophorylated-Ser202/204. beta-Actin was a control to make sure all lanes are loaded with same amount of protein. The western blot demonstrated that at 10 ug/ml (2 uM), Peptide SEQ ID No:1 significantly inhibits phosphorylation of Erk1/2, which is downstream of Ras-Raf pathway.

---

What is claimed:

1. A peptide consisting of the sequence of SEQ ID NO:1.

2. A pharmaceutical composition for treatment of human or animal tissue fibrosis, wherein the pharmaceutical composition comprises the peptide according to claim 1 and a pharmaceutically acceptable carrier.

3. The pharmaceutical composition according to claim 2, wherein the pharmaceutical composition further comprises other medicine which treat human or animal tissue fibrosis.

4. The pharmaceutical composition according to claim 2, wherein the pharmaceutical composition is in the form of oral dosage, subcutaneous injection dosage, intradermal injection dosage, intramuscular injection dosage, intravenous injection dosage and nasal dosage.

5. A pharmaceutical composition for treatment of human or animal cancers, wherein the pharmaceutical composition comprises the peptide according to claim 1 and a pharmaceutically acceptable carrier, wherein the cancer is selected from the group consisting of lung cancer, liver cancer, breast cancer and stomach cancer.

6. The pharmaceutical composition according to claim 5, wherein the pharmaceutical composition further comprises other medicine which treat human or animal cancers.

7. The pharmaceutical composition according to claim 5, wherein the pharmaceutical composition further comprise other chemotherapy agents.

8. The pharmaceutical composition according to claim 5, wherein the pharmaceutical composition further comprises Gleevec.

9. A method for treatment of human or animal tissue fibrosis comprising administering a peptide consisting of the amino acid sequence of SEQ ID NO: 1.

10. The method of claim 9, wherein the tissue comprises human or animal liver, kidney or lung.

11. A method for the treatment of human or animal primary cancers and cancer metastasis comprising administering to the human or animal having a primary cancer or cancer metastasis a peptide consisting of the amino acid sequence of SEQ ID NO: 1, wherein the cancer is selected from the group consisting of lung cancer, liver cancer, breast cancer and stomach cancer.

12. A method of administering pharmaceutical composition according to claim 2, comprising the step of administering a peptide, wherein the peptide consists of SEQ ID NO: 1 sequence, comprising administering the peptide intramuscularly, intravenously, subcutaneously, orally, rectally, and percutaneoulsy.

* * * * *

UNITED STATES PATENT AND TRADEMARK OFFICE
CERTIFICATE OF CORRECTION

PATENT NO. : 8,637,467 B2  
APPLICATION NO. : 13/123424  
DATED : January 28, 2014  
INVENTOR(S) : Huang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this
Twenty-first Day of July, 2015

Michelle K. Lee
*Director of the United States Patent and Trademark Office*